(12) United States Patent
Pesti et al.

(10) Patent No.: US 6,214,847 B1
(45) Date of Patent: Apr. 10, 2001

(54) CRYSTALLINE 10,10-BIS((2-FLUORO-4-PYRIDINYL)METHYL)-9(10H)-ANTHRACENONE AND AN IMPROVED PROCESS FOR PREPARING THE SAME

(75) Inventors: Jaan A. Pesti, Wilmington; Joseph M. Fortunak; George F. Huhn, both of Newark; Michael Maurin, Wilmington; Jianguo Yin, Hockessin, all of DE (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/131,953

(22) Filed: Aug. 11, 1998

Related U.S. Application Data

(60) Provisional application No. 60/080,223, filed on Aug. 14, 1997, and provisional application No. 60/077,395, filed on Mar. 10, 1998.

(51) Int. Cl.[7] .......................... A61K 31/44; C07D 401/02
(52) U.S. Cl. ............................. 514/332; 546/255
(58) Field of Search .................. 546/255; 514/332

(56) References Cited

U.S. PATENT DOCUMENTS

| | | | |
|---|---|---|---|
| 5,296,478 | 3/1994 | Teleha | 514/235.2 |
| 5,594,001 | 1/1997 | Teleha et al. | 514/290 |

FOREIGN PATENT DOCUMENTS 0557967  9/1993  (EP) .

OTHER PUBLICATIONS

Bovonsombat et al., *Synthesis*, Ring Halogenations of Polyalkylbenzenes with N–Halosuccinimide and Acidic Catalysts, (1993), pp. 237–241.

Carreño et al., *J. Org. Chem.*, (1995), 60, N–Bromosuccinimide in Acetonitrile: A Mild and Regiospecific Nuclear Brominating Reagent for Methoxybenzenes and Naphthalenes, pp. 5328–5311.

Adam et al., *Nature*, (1953), 171, "Laws of Addition and Substitution in Atomic Reactions of Halogens", pp. 704–705.

Thomas Oberhauser, *J. Org. Chem.*, (1997), 62, "A New Bromination Method for Phenols and Anisoles: NBS/HBF$_4$—Et$_2$O in CH$_3$CN", pp. 4504–4506.

Paul et al., *Tetrahedron Letters*, (1994) vol. 35, 38, "Regioselective Bromination of Activated Aromatic Substrates with N–Bromosuccinimide over HZSM–5", pp. 7055–7056.

*Primary Examiner*—Zinna Northington Davis
(74) *Attorney, Agent, or Firm*—Peter L. Dolan

(57) ABSTRACT

The present invention relates to processes for the synthesis of a crystalline polymorph of 10,10-Bis((2-fluoro-4-pyridinyl)methyl)-9(10H)-Anthracenone in high purity. The product is useful in the synthesis of pharmaceutical compounds for the reduction of cholinergic system dysfunction.

8 Claims, 3 Drawing Sheets

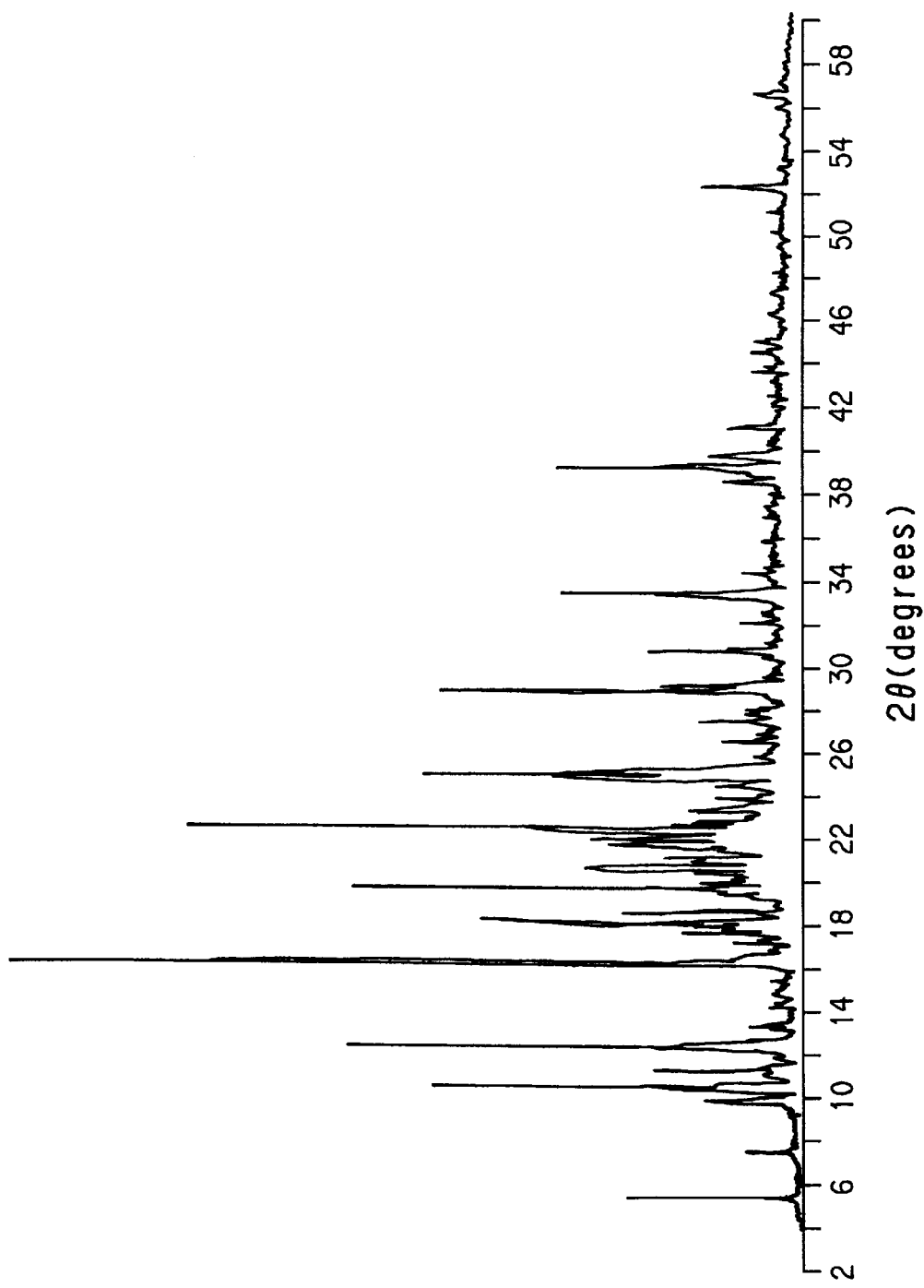

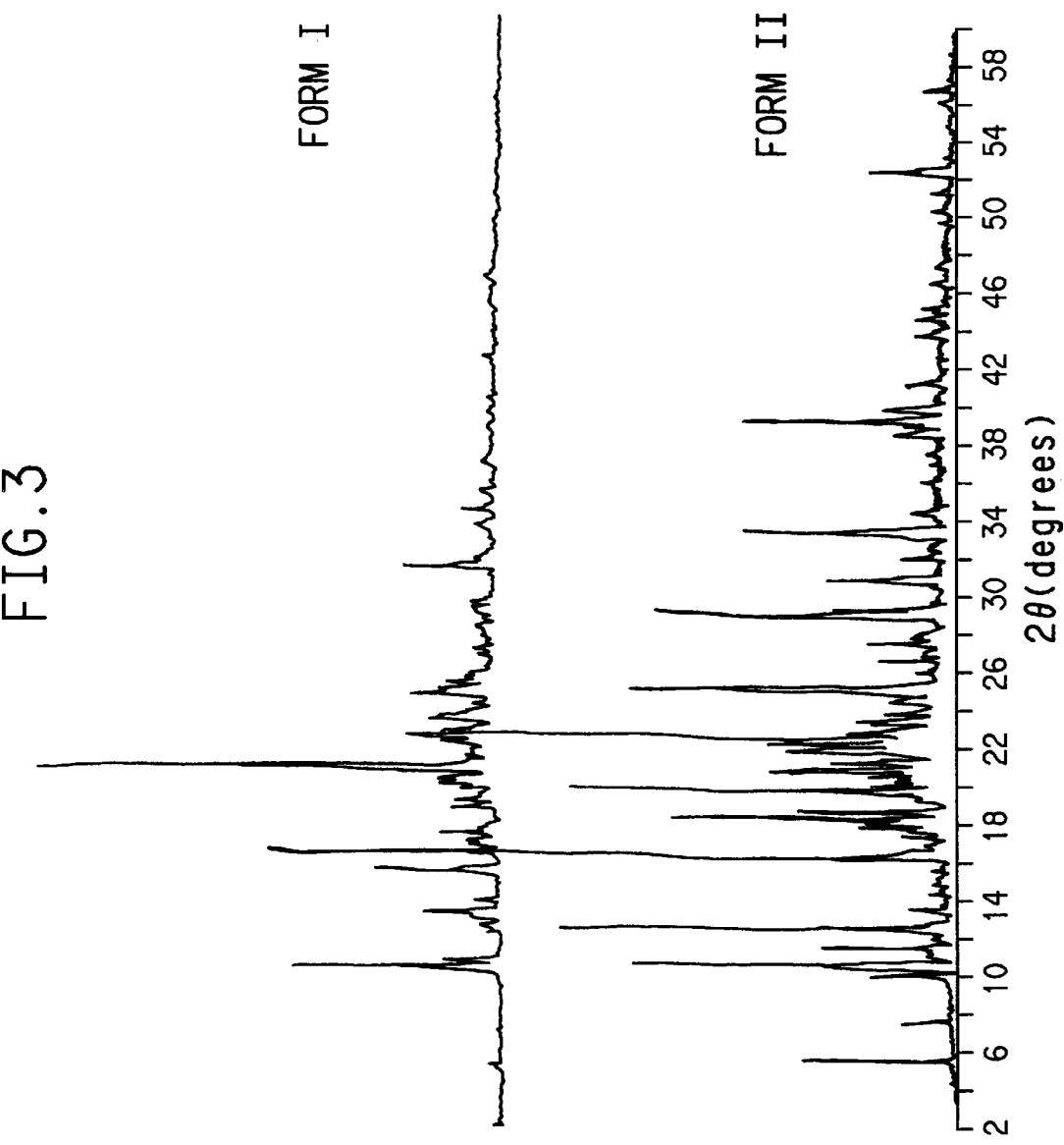

CRYSTALLINE 10,10-BIS((2-FLUORO-4-PYRIDINYL)METHYL)-9(10H)-ANTHRACENONE AND AN IMPROVED PROCESS FOR PREPARING THE SAME

This application claims the benefit of U.S. Provisional Application No. 60/080,223 filed Aug. 14, 1997; and U.S. Provisional Application No. 60/077,395, filed Mar. 10, 1998.

FIELD OF THE INVENTION

This invention relates to processes for the synthesis of a stable polymorph of crystalline 10,10-bis((2-fluoro-4-pyridinyl)methyl)-9(10H)-Anthracenone in high purity. The product is useful in the synthesis of compounds for pharmaceuticals, especially pharmaceuticals for the reduction of cholinergic system dysfunction.

BACKGROUND OF THE INVENTION

Alzheimer's disease is the most common type of dementia experienced in the developed world. It is a devastating illness whose prevalence increases dramatically with age; first appearing around 40 in some and rising to perhaps 50% of the population to some degree by age 85. (D. Evans, *Milbank Q*, 1990, 68, 267–289). Alzheimer's disease manifests itself by insidiously destroying memory and leading to mental confusion as nerve cells in the brain are relentlessly lost. The general aging of the population in the coming years will increase the prevalence of the disease and emphasize the need to ameliorate these medical needs before it reaches epidemic proportions.

Research has led to the examination of a variety of drug strategies, largely without success. Early therapeutic strategies include those that were reputed to improve cerebral blood flow or possess psychostimulant abilities. These include the metabolic enhancer dihydroergotoxine, the vasodilators papaverine, isoxsuprine, and cyclandelate, and the psychostimulants methylphenidate and pentylenetetrazol. (W. H. Moos, R. E. Davis, R. D. Schwarz, and E. R. Gamzu, *Medicinal Resarch Reviews*, Vol. 8, No. 3, 353–391 (1988)). None of these are reported to possess any significant effect upon the disease.

While a variety of classes of therapeutics such as muscarinic receptor agonists, nootropics, nicotinic agonists, m1 agonists and $Ca^{++}$ channel blockers are in various stages of development, of greater interest and potential value are the cholinergic agents including acetylcholinesterase inhibitors, acetylcholine release precursors and storage modulators. This 'cholinergic deficiency', hypothesis has dominated research over the past two decades since of all the neurotransmitters, acetylcholine is known to exhibit the greatest decrease in Alzheimer's patients and it has long been connected to learning and memory.

Only two drugs have approval by the FDA for clinical use; the cholinesterase inhibitors Cognex® (tacrine or tetrahydroaminacrine) and Aricept® (donepezil). Tacrine has been marketed for several years but its initial promise has largely been unfulfilled (Hollister, L.; Gruber, N. *Drugs and Aging* 1996, 8, 47–55). However, benefits that were noted with tacrine appear to supply support for the cholinergic hypothesis of Alzheimer's disease. ( M. R. Farlow, *Alzhemier Disease and Associated Disorders*, 1994,8, Suppl. 2, S50–S57). Donepezil has very recently been granted approval and is still undergoing evaluation in the general population (Kawakami, Y.; Inoue, A.; Kawai, T.; Wakita, M.; Sugimoto, H. Hopfinger, A. J. *Bioorganic & Med, Chem. Lett*. 1996, 4, 1429–1445).

The DuPont Merck Pharmaceutical Company initiated a major research effort in the early 1980s to identify compounds that enhanced neurotransmitter release. This led to a novel class of compounds highlighted by linopirdine which underwent clinical examination, (review of linopirdine: Chorvat et al. *Drugs of the Future* 1995, 20(11), 1145–162). Compound I is representative of second generation compounds discovered in this continuing area of research.

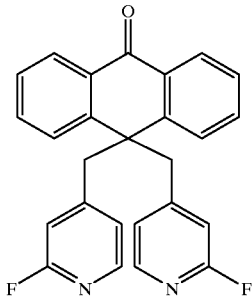

I

International publication WO 94/241131 (Teleha, C. A.; Wilkerson, W. W.; Earl, R. A.) and International publication WO 95/27489 (Saydoff, J., Zaczek, R.) indicate the value of I as a acetylcholine release agent and as possibly useful in the treatment of cognitive and learning disorders. Due to the importance of Compound I in the treatment of cognitive diseases, it is necessary to develop economical and efficient synthetic processes for its production.

The utility of the present invention lies in the discovery of an efficient process that permits the commercial manufacture of a more stable Form 2 polymorph of crystalline I. U.S. Pat. No. 5,594,001 (Teleha, C. A.; Wilkerson, W. W.; Earl, R. A.) teaches that I may be prepared by the initial chlorination of 2-fluoro-4-methylpyridine to the monochloro product followed by its use for the bis-alkylation of anthrone. The process described by Teleha, et al. requires the use of the solvent carbon tetrachloride (expensive, an environmental hazard and a suspected carcinogen) to generate the benzyl chloride. Additionally, repeated column chromatography is necessary to purify the drug. This method is not realistically scalable to multi-kilo preparations.

The present invention provides for a more efficient, non-chromatographic purification process to yield a stable, crystalline product without the use of dangerous, costly materials. The process employs the use of acetonitrile as a safer, more economical alternative to carbon tetrachloride. A significant improvement also stems from the discovery that through the use of catalytic acid, the chlorination is faster and generates less impurities when compared to the same reaction without acid. This result was unexpected in light of the literature which teaches that the use of N-bromosuccinimide in the presence of acid results in ring halogenation as opposed to sidechain halogenation (Bovonsombat and McNelis, *Synthesis*, 1993, 237–241). The chlorinated product is then converted to the water soluble benzyl alcohol derivative allowing separation from unchlorinated or overchlorinated impurities which are characteristic by-products of such a system. The present invention proceeds through a stable, crystalline mesylate intermediate, which removes the need for chromatographic separation prior to alkylation with anthrone. Dialkylation of anthrone with the mesylate intermediate in the presence of strong base provides the final drug. Recrystallization in alcoholic solvents leads to a more thermodynamically stable polymorph which is extremely advantageous to the commercial scale manufacture of this important compound.

SUMMARY OF THE INVENTION

The present invention concerns novel processes for the preparation of a crystalline polymorphs of a substituted anthrone which is useful in the treatment of cognitive disorders.

BRIEF DESCRIPTION OF THE DRAWINGS

The invention is illustrated by reference to the accompanying drawings described below.

FIG. 2 shows a powder x-ray diffractogram of the Form 2 crystalline polymorph of 10,10-Bis((2-fluoro-4-pyridinyl)methyl)-9(10H)-anthracenone.

FIG. 3 shows powder x-ray diffractograms of Form 1 and Form 2 polymorphs of 10,10-Bis((2-fluoro-4-pyridinyl)methyl)-9(10H)-anthracenone.

DETAILED DESCRIPTION OF THE INVENTION

Figure 1:
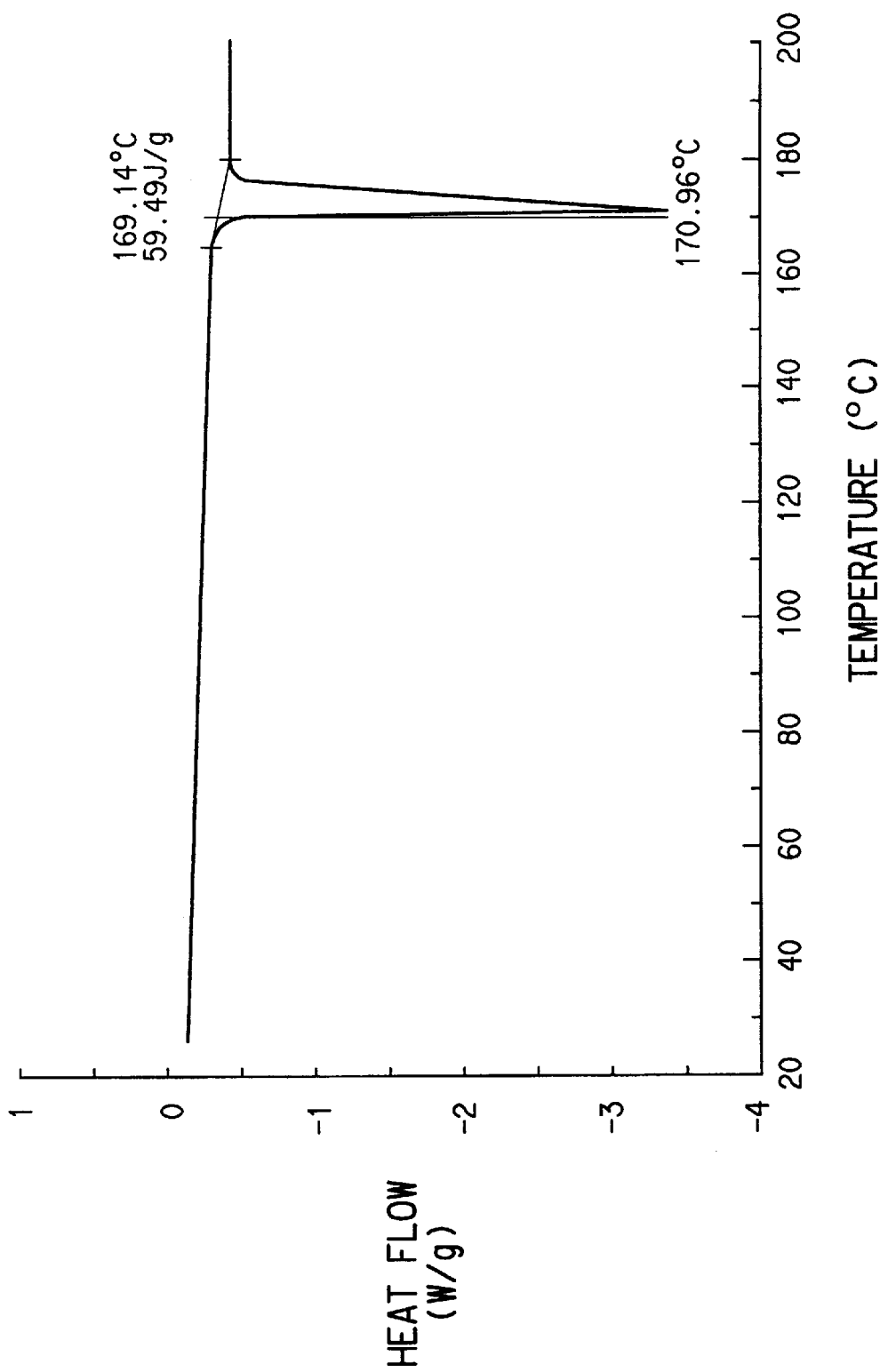
FIG. 1 shows a differential calorimetry thermogram of the Form 2 crystalline polymorph of 10,10-Bis((2-fluoro-4-pyridinyl)methyl)-9(10H)-anthracenone.

In a first embodiment, the present invention provides a novel process for the preparation of a compound of formula (I):

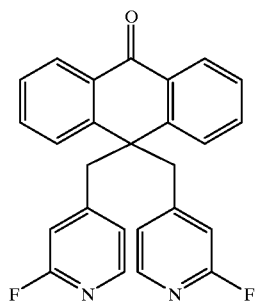

I said process comprising:

(1) contacting, for a sufficient amount of time, at a suitable temperature, a compound of formula (II):

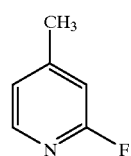

II in acetonitrile with about one equivalent of a suitable halogenating agent in the presence of a suitable radical initiator to form a mixture of compounds of formula (II), (III) and (IV):

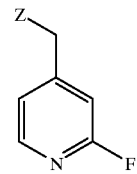

III

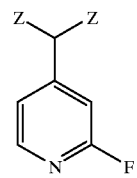

IV wherein Z is chlorine or bromine;

(2) contacting the mixture of compounds II, III and IV from Step 1 with water containing at least one equivalent of a suitable base to form a compound of formula (V):

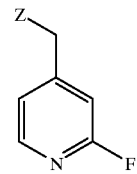

V (3) extracting the solution from Step 2 with a suitable extraction solvent to remove compounds of formula (II) and (IV);

(4) extracting the resultant aqueous solution from Step 3 with a suitable polar organic solvent to remove compound (V);

(5) contacting a compound of formula (V) with a suitable sulfonylating agent in the presence of a suitable acid scavanger to give a compound of formula (VI):

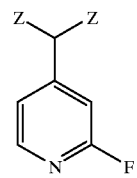

VI wherein —OA is a sulfonate ester;

(6) contacting a compound of formula (VI) with a suitable iodine salt in a suitable reaction solvent to give a compound of formula (VII):

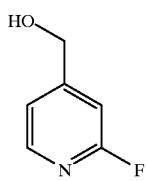

VII and (7) contacting a compound of formula (VIII):

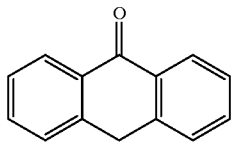

VIII in the presence of a suitable strong base with a compound of formula (VII) to provide a compound of formula (I).

In a preferred embodiment for the preparation of a compound of formula (I):
A is selected from the group:
   methanesulfonyl, trifluorosulfonyl, p-toluenesulfonyl and benzenesulfonyl;
the sufficient amount of time is about 1 to about 8 hours;
the suitable temperature is about 40° C. to about 100° C.;
the suitable halogenating agent is selected from the group: N-chlorosuccinimide, N-bromosuccinimide, chlorine, and bromine;
the suitable radical initiator is benzoyl peroxide or 2,2'-azobisisobutyronitrile;
the suitable base is selected from the group:
   $Li_2CO_3$, $K_2CO_3$, $Na_2CO_3$, $Cs_2CO_3$, NaOH, KOH, and LiOH;
the suitable extraction solvent is selected from the group:
   pentane, hexane, heptane, benzene, and toluene;
the suitable polar organic solvent is selected from the group:
   methyl acetate, ethyl acetate, propyl acetate and isopropyl acetate;
the suitable acid scavenger is selected from the group:
   triethyl amine, N-methylmorpholine, pyridine and diisopropylethylamine;
the suitable iodine salt is selected from the group:
   NaI, KI, LiI and tetrabutylammonium iodide;
the suitable reaction solvent is acetone or tetrahydrofuran; and,
the suitable strong base is selected from the group:
   lithium t-butoxide, sodium t-butoxide, potassium t-butoxide, isobutyllithium, n-hexyllithium, n-octyllithium, n-butyllithium, s-butyllithium, t-butyllithium, phenyllithium, triphenylmethyllithium, sodium amide, potassium amide, lithium amide, sodium hydride, potassium hydride, lithium hydride, lithium hexamethyl disilazide, sodium hexamethyl disilazide and potassium hexamethyl disilazide.

In a more preferred embodiment for the preparation of a compound of formula (I):
A is selected from the group:
   methanesulfonyl, trifluoromethylsulfonyl or p-toluene sulfonyl;
the sufficient amount of time is about 1 to about 8 hours;
the suitable temperature is about 40° C. to about 100° C.;
the suitable halogenating agent is N-chlorosuccinimide or chlorine;
the suitable radical initiator is benzoyl peroxide or 2,2'-azobisisobutyronitrile;
the suitable base is selected from the group:
   $Li_2CO_3$, $K_2CO_3$ and $Na_2CO_3$;
the suitable extraction solvent is selected from the group:
   pentane, hexane and heptane;
the suitable polar organic solvent is selected from the group:
   methyl acetate, ethyl acetate and isopropyl acetate;
the suitable acid scavenger is triethyl amine or diisopropylethylamine;
the suitable iodine salt is selected from the group:
   sodium iodide, lithium iodide and potassium iodide;
the suitable reaction solvent is tetrahydrofuran;
the suitable strong base is selected from the group:
   lithium t-butoxide, sodium t-butoxide, potassium t-butoxide, n-butyllithium, t-butyllithium, sodium amide, potassium amide, lithium amide, sodium hydride, potassium hydride, lithium hydride, lithium hexamethyl disilazide, sodium hexamethyl disilazide and potassium hexamethyl disilazide.

In an even further more preferred embodiment for the preparation of a compound of formula (I):
A is methanesulfonyl;
the sufficient amount of time is about 5 to about 8 hours;
the suitable temperature is about 50° C. to about 80° C.;
the suitable halogenating agent is N-chlorosuccinimide;
the suitable radical initiator is benzoyl peroxide;
the suitable base is $Na_2CO_3$;
the suitable extraction solvent is hexane;
the suitable polar organic solvent is ethyl acetate;
the suitable acid scavenger is triethylamine;
the suitable iodine salt is NaI;
the suitable reaction solvent is tetrahydrofuran;
the suitable strong base is lithium t-butoxide.

In a second embodiment, the present invention provides a process for the preparation of a mixture of compounds of formula (II), (III), and (IV), said process comprising:
(1) contacting, for a sufficient amount of time, at a suitable temperature, a compound of formula (II) with approximately one equivalent of a suitable halogenating agent in acetonitrile in the presence of a suitable radical initiator and a catalytic amount of a suitable acid to form a mixture of compounds of the formula (II), (III) and (IV).

A preferred embodiment for the preparation of a mixture of compounds of formula (II), (III), and (IV), comprises:
(1) contacting, for about 1 to about 4 hours, at about 40° C. to about 100° C., a compound of formula (II) with approximately one equivalent of N-chlorosuccinimide, N-bromosuccinimide, chorine, or bromine in acetonitrile in the presence of benzoyl peroxide or 2,2'-azobisisobutyronitrile and a catalytic amount of HCl, methanesulfonic acid, p-toluene sulfonic acid, benzenesulfonic acid, phosphoric acid, acetic acid, sulfuric acid or trifluoroacetic acid to form a mixture of compounds of the formula (II), (III) and (IV).

A more preferred embodiment for the preparation of a mixture of compounds of formula (II), (III), and (IV), comprises:
(1) contacting, for about 1 to about 4 hours, at about 40° C. to about 100° C., a compound of formula (II) with approximately one equivalent of N-chlorosuccinimide or chlorine in acetonitrile in the presence of benzoyl peroxide or 2,2'-azobisisobutyronitrile and a catalytic amount of HCl, methanesulfonic acid, p-toluene sulfonic acid, acetic acid, sulfuric acid or trifluoroacetic acid to form a mixture of compounds of the formula (II), (III) and (IV).

An even more preferred embodiment for the preparation of a mixture of compounds of formula (II), (III), and (IV), comprises:
(1) contacting, for about 1 to about 3 hours, at about 40° C. to about 80° C., a compound of formula (II) with approximately one equivalent of N-chlorosuccinimide in acetonitrile in the presence of benzoyl peroxide and a catalytic amount of acetic acid to form a mixture of compounds of the formula (II), (III) and (IV).

In a third embodiment the present invention provides a process for the preparation of a compound of formula (V), said process comprising:

(1) contacting a mixture of compounds of formula (II), (III) and (IV) with water containing at least one equivalent of a suitable base to form a compound of the formula (V);

(2) extracting the solution from Step 1 with a suitable extraction solvent to remove compounds of formula (II) and (IV); and (3) extracting the resultant aqueous solution from Step 2 with a suitable polar organic solvent to remove the compound of formula (V).

In a preferred embodiment for the preparation of a compound of formula (V):
the suitable base is selected from the group:
sodium hydroxide, lithium hydroxide, potassium hydroxide, lithium carbonate, sodium carbonate, potassium carbonate, and cesium carbonate
the suitable extraction solvent is selected from the group: pentane, hexane, heptane, benzene, and toluene; and
the suitable polar organic solvent is selected from the group: methyl acetate, ethyl acetate, propyl acetate and isopropyl acetate.

In a more preferred embodiment for the preparation of a compound of formula (V):
the suitable base is selected from the group:
lithium carbonate, sodium carbonate, potassium carbonate;
the suitable extraction solvent is selected from the group: pentane, hexane, and heptane; and
the suitable polar organic solvent is ethyl acetate.

In an further more preferred embodiment for the preparation of a compound of formula (V):
the suitable base is $K_2CO_3$;
the suitable extraction solvent is hexane; and
the suitable polar organic solvent is ethyl acetate.

In a fourth embodiment, the present invention provides a process for the preparation of a compound of formula (V), said process comprising:

(1) contacting, for a sufficient amount of time, at a suitable temperature, a compound of formula (II) with approximately one equivalent of a suitable halogenating agent in the presence of a suitable radical initiator to form a mixture of compounds of the formula (II), (III) and (IV);

(2) contacting the mixture from Step 1 with water containing at least one equivalent of a suitable base to form a compound of the formula (V);

(3) extracting the solution from Step 2 with a suitable extraction solvent to remove compounds of formula (II) and (IV); and (4) extracting the resultant aqueous solution from Step 3 with a suitable polar organic solvent to remove the compound of formula (V).

In a preferred embodiment for the preparation of a compound of formula (V):
the sufficient amount of time is about 1 to about 4 hours;
the suitable temperature is about 40° C. to about 100° C.;
the suitable halogenating agent is selected from the group: N-chlorosuccinimide, N-bromosuccinimide, chlorine and bromine;
the suitable radical initiator is benzoyl peroxide or 2,2'-azobisisobutyronitrile;
the suitable base is selected from the group:
sodium hydroxide, lithium hydroxide, potassium hydroxide, lithium carbonate, sodium carbonate, potassium carbonate, and cesium carbonate;
the suitable extraction solvent is selected from the group: pentane, hexane, heptane, benzene, and toluene; and
the suitable polar organic solvent is selected from the group: methyl acetate, ethyl acetate, propyl acetate and isopropyl acetate.

In a more preferred embodiment for the preparation of a compound of formula (V):
the sufficient amount of time is about 1 to about 4 hours;
the suitable temperature is about 40° C. to about 100° C.;
the suitable halogenating agent is N-chlorosuccinimide or chlorine;
the suitable radical initiator is benzoyl peroxide or 2,2'-azobisisobutyronitrile;
the suitable base is selected from the group:
lithium carbonate, sodium carbonate and potassium carbonate;
the suitable extraction solvent is selected from the group: pentane, hexane, and heptane; and
the suitable polar organic solvent is ethyl acetate.

In an even more preferred embodiment for the preparation of a compound of formula (V):
the sufficient amount of time is about 1 to about 3 hours;
the suitable temperature is about 50° C. to about 80° C.;
the suitable halogenating agent is N-chlorosuccinimide;
the suitable radical initiator is benzoyl peroxide;
the suitable base is $K_2CO_3$;
the suitable extraction solvent is hexane; and
the suitable polar organic solvent is ethyl acetate.

In a fifth embodiment, the present invention provides the Form 2 polymorph of crystalline 10,10-Bis((2-fluoro-4-pyridinyl)methyl)-9(10H)-anthracenone.

In a preferred embodiment, the Form 2 polymorph of crystalline 10,10-Bis((2-fluoro-4-pyridinyl)methyl)-9(10H)-anthracenone is in substantially pure form.

In a more preferred embodiment, the Form 2 polymorph of crystalline 10,10-Bis((2-fluoro-4-pyridinyl)methyl)-9(10H)-anthracenone in substantially pure form has a purity greater than 90 percent.

In another preferred embodiment, the Form 2 polymorph of crystalline 10,10-Bis((2-fluoro-4-pyridinyl)methyl)-9(10H)-anthracenone, is characterized by an x-ray powder diffraction pattern comprising of 2θ values of 5.8±0.2, 7.8±0.2, 10.7±0.2, 12.6+0.2, 16.4±0.2, 18.3±0.2, 19.8±0.2, 22.5±0.2, 24.9±0.2, 28.9±0.2, and 39.1±0.2.

In another preferred embodiment, the Form 2 polymorph of crystalline 10,10-Bis((2-fluoro-4-pyridinyl)methyl)-9(10H)-anthracenone is characterized by an x-ray powder diffraction pattern substantially in accordance with that shown in FIG. 2.

In another preferred embodiment, the Form 2 polymorph of crystalline 10,10-Bis((2-fluoro-4-pyridinyl)methyl)-9(10H)-anthracenone is characterized by a differential scanning calorimetry thermogram having a peak at about 168° C. to about 172° C.

In another preferred embodiment, the Form 2 polymorph of crystalline 10,10-Bis((2-fluoro-4-pyridinyl)methyl)-9(10H)-anthracenone is characterized by a differential scanning calorimetry thermogram substantially in accordance with that shown in FIG. 1.

In a more preferred embodiment, the Form 2 polymorph of crystalline 10,10-Bis((2-fluoro-4-pyridinyl)methyl)-9(10H)-anthracenone is characterized by an x-ray powder diffraction pattern comprising of 2θ values of 5.8±0.2, 7.8±0.2, 10.7±0.2, 12.6±0.2, 16.4±0.2, 18.3±0.2, 19.8±0.2, 22.5±0.2, 24.9±0.2, 28.9±0.2, and 39.1±0.2, and further characterized by a differential scanning calorimetry thermogram having a peak at about 168° C. to about 172° C.

In another more preferred embodiment, the Form 2 polymorph of crystalline 10,10-Bis((2-fluoro-4-pyridinyl)methyl)-9(10H)-anthracenone is characterized by an x-ray powder diffraction pattern comprising of 2θ values of 5.8±0.2, 7.8±0.2, 10.7±0.2, 12.6±0.2, 16.4±0.2, 18.3±0.2, 19.8±0.2, 22.5±0.2, 24.9±0.2, 28.9±0.2, and 39.1±0.2, and further characterized by a differential scanning calorimetry thermogram substantially in accordance with FIG. 1.

In another more preferred embodiment, the Form 2 polymorph of crystalline 10,10-Bis((2-fluoro-4-pyridinyl) methyl)-9(10H)-anthracenone is characterized by an x-ray powder diffraction pattern substantially in accordance with FIG. 2, and further characterized by a differential scanning calorimetry thermogram having a peak at about 168° C. to about 172° C.

In a sixth embodiment, the present invention describes a pharmaceutical composition which comprises a therapeutically effective amount of crystalline 10,10-Bis((2-fluoro-4-pyridinyl)methyl)-9 (10H)-anthracenone and a pharmaceutically acceptable carrier.

In a seventh embodiment, the present invention describes a pharmaceutical composition in solid unit dosage form which comprises a therapeutically effective amount of crystalline 10,10-Bis((2-fluoro-4-pyridinyl)methyl)-9(10H)-anthracenone and a pharmaceutically acceptable carrier.

In a preferred embodiment, the solid unit dosage form contains about 0.025 mg to about 100 mg of the Form 2 polymorph of crystalline 10,10-Bis((2-fluoro-4-pyridinyl) methyl)-9(10H)-anthracenone per unit dose.

In an eighth embodiment, the present invention describes a method for the treatment of cognitive or neurological dysfunction comprising administering to a host in need thereof a therapeutically effective amount of the Form 2 polymorph of crystalline 10,10-Bis((2-fluoro-4-pyridinyl) methyl)-9(10H)-anthracenone.

In a ninth embodiment, the Form 2 polymorph of crystalline 10,10-Bis((2-fluoro-4-pyridinyl)methyl)-9(10H)-anthracenone is prepared by recrystallization from an alcoholic solvent.

In a preferred embodiment, the Form 2 polymorph of crystalline 10,10-Bis((2-fluoro-4-pyridinyl)methyl)-9 (10H)-anthracenone is recrystallized from isopropanol.

In a tenth embodiment, the present invention describes the Form 2 polymorph of crystalline 10,10-Bis((2-fluoro-4-pyridinyl)methyl)-9(10H)-anthracenone, prepared by the steps of:

(1) Dissolving 10,10-bis((2-fluoro-4-pyridinyl) methyl)-9 (10H)-anthracenone in a suitable amount of an alcoholic solvent to a suitable dissolution temperature;

(2) cooling the solution from step (1) to a suitable crystallization temperature to effect the precipitation of the Form 2 polymorph; and (3) isolating the crystals from step (2) in substantially pure form.

In a preferred embodiment for the preparation of the Form 2 polymorph of crystalline 10,10-Bis((2-fluoro-4-pyridinyl) methyl)-9(10H)-anthracenone:
the suitable alcoholic solvent is isopropanol;
the suitable dissolution temperature is from about 40° C. to about 84° C.;
the suitable crystallization temperature is about −5° C. to about 40° C.; and
substantially pure form comprises a Form 2 polymorph with a purity greater than 90 percent.

DEFINITIONS

The following terms and abbreviations are used herein and defined as follows. The abbreviation: "THF" as used herein means tetrahydrofuran, "EtOAc" as used herein means ethyl acetate, "HPLC" as used herein means high performance liquid chromatograpy, "TLC" as used herein means thin layer chromatography, "eq" as used herein means equivalent(s), "NCS" as used herein means N-chlorosuccinimide, "NBS" as used herein means N-bromosuccinimide, "AIBN" as used herein means 2,2'-azobisisobutyronitrile, "t-BuOK" as used herein means potassium tert-butoxide. "DSC" as used herein means differential scanning calorimetry.

The reactions of the synthetic methods claimed herein are carried out in suitable reaction solvents which may be readily selected by one of skill in the art of process chemistry, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. When a reaction solvent is chosen, it is determined independently from, and not limited by, solvents chosen for other reactions. Examples of "suitable reaction solvents" include but are not limited to acetonitrile, ethyl acetate, dimethylsulfoxide, N,N-dimethylformamide, acetone, N,N-dimethylacetamide, carbon tetrachloride, dichloroethane, chloroform, chlorobutane, hydrocarbons, ethers and aryls, wherein "hydrocarbons" are butane, pentane, hexane, heptane, octane, nonane, decane, cyclohexane, cycloheptane, methylcyclohexane; wherein ether solvents are tetrahydrofuran, 1,4 dioxane, diethyl ether, diethoxymethane, ethylene glycol dimethyl ether, ethylene glycol diethyl ether, diethylene glycol dimethyl ether, diethylene glycol diethyl ether, triethylene glycol dimethyl ether and t-butyl methyl ether; and wherein aryl solvents are benzene, toluene, ethylbenzene, o-xylene, m-xylene and p-xylene.

The products and intermediates of the present invention may be recrystallized in suitable solvents which may be readily selected by one of skill in the art of organic synthesis. Suitable solvents include those in which the final product is reasonably soluble, having a boiling point which is lower than the melting point of the solid compound. The final compounds of the present invention may be recrystallized in any suitable solvents which result in the formation of the Form 2 polymorph. Suitable recrystallization solvents include alcoholic solvents, wherein alcoholic solvents include but are not limited to methanol, ethanol, propanol, 2-propanol, butanol, iso-butanol, sec-butanol, t-butanol, pentanol and hexanol.

As used herein, "suitable halogenating agents" are those known in the art of organic synthesis capable of donating a halogen to the benzyl position in radical reactions. Such agents include but are not limited to chlorine, bromine, N-chlorosuccinimide and N-bromosuccinimide.

As used herein, "suitable radical initiators" are those known in the art of organic synthesis to spontaneously form free radicals. Examples of such include, but are not limited to benzoyl peroxide, 2,2'-Azobisisobutyronitrile (AIBN), di-tert-butyl peroxide and tert-butyl peroxybenzoate.

As used herein, "suitable base" refers to any base capable of dissolving in water and accepting a proton from a protonated alcohol. Examples of such include but are not limited to lithium, sodium, potassium and cesium carbonate; sodium bicarbonate; lithium, sodium, potassium, calcium and magnesium hydroxide.

As used herein, "suitable sulfonylating agents" are any known in the art of organic synthesis to react with an alcohol to give a sulfonate ester. Examples of such include, but are not limited to methanesulfonyl chloride, methanesulfonic anhydride, trifluoromethane sulfonyl chloride, trifluoromethane sulfonic anhydride, benzene sulfonyl chloride, p-toluenesulfonyl chloride, and p-toluenesulfonic anhydride.

As used herein, a "sulfonate ester" is a group which results when a sulfonating agent is reacted with an alcohol in the presence of an acid scavenger to give a compound of form —O—A, wherein A=$SO_2$R, with R deriving from the sulfonylating agent.

As used herein, a "suitable acid scavenger" refers to any species known in the art of organic synthesis capable of accepting a proton without reacting with the starting material or product. Examples include but are not limited to amines such as trimethylamine, triethylamine, N-methylmorpholine, diisopropylethylamine, pyridine and piperidine.

As used herein, "suitable iodine salts" include but are not limited to lithium iodide, sodium iodide, potassium iodide, tetramethylammonium iodide and tetrabutylammonium iodide.

As used herein, the term "strong base" refers to any agent which effects the deprotonation of the anthrone at the 10 position. Examples of such strong bases include, but are not limited to, alkoxides, alkyllithiums, metal amides, metal hydrides, metal dialkylamides and arylamines, wherein; alkoxides include lithium, sodium and potassium salts of methyl, ethyl and t-butyl oxides; alkyllithiums include, isobutyllithium, n-hexyllithium, n-octyllithium, n-butyllithium, s-butyllithium, t-butyllithium, phenyllithium and triphenylmethyllithium; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

As used herein, "suitable acid" refers to any agent capable of donating a proton to an aromatic ring nitrogen in an organic solvent. Examples include but are not limited to hydrochloric acid, hydrobromic acid, sulfuric acid, phosphoric acid, nitric acid, formic acid, acetic acid, propionic acid, butanoic acid, methanesulfonic acid, p-toluene sulfonic acid, benzenesulfonic acid and trifluoroacetic acid.

As used herein, "suitable extraction solvents" include, by way of example and without limitation, hydrocarbon, ether and aryl solvents. "Suitable hydrocarbon solvents" include: butane, pentane, hexane, heptane, octane, nonane, decane, cyclohexane, cycloheptane, methylcyclohexane; suitable ether solvents include: diethyl ether, diethoxymethane, ethylene glycol dimethyl ether, ethylene glycol diethyl ether, diethylene glycol dimethyl ether, diethylene glycol diethyl ether, triethylene glycol dimethyl ether and t-butyl methyl ether. Suitable aryl solvents include benzene, toluene, ethylbenzene, o-xylene, m-xylene and p-xylene.

As used herein, "suitable polar organic solvents" are those capable of extracting benzyl alcohol derivatives from aqueous solutions. Examples include but are not limited to methyl, ethyl, propyl and iso-propyl acetate, methylene chloride, chloroform, n-butyl chloride and dichloroethane.

As used herein, "suitable organic solvents" are those that are immiscible with water and capable of dissolving organic constituents. Examples include, but are not limited to dichloroethane, chloroform, chlorobutane, hydrocarbons, ethers and aryls, wherein hydrocarbons are butane, pentane, hexane, heptane, octane, nonane, decane, cyclohexane, cycloheptane, methylcyclohexane; wherein ethers are diethyl ether, diethoxymethane, ethylene glycol dimethyl ether, ethylene glycol diethyl ether, diethylene glycol dimethyl ether, diethylene glycol diethyl ether, triethylene glycol dimethyl ether and t-butyl methyl ether; and wherein aryls are benzene, toluene, ethylbenzene, o-xylene, m-xylene and p-xylene.

The term "pharmaceutical composition" as used herein refers to a composition comprised of a compound and a pharmaceutical carrier selected on the basis of the chosen route of administration and standard pharmaceutical practice.

The term "therapeutically effective" as used herein and in the claims refers to that amount of a compound of formula (I) necessary to enhance the residual function of the affected systems by enhancing the stimulus-induced release of neurotransmitters thereby reducing deficits in processes related to cognition, neurological function, and mood regulation.

The term "therapeutically effective amount" as used herein is intended to mean that amount useful for the treatment of cognitive disorders and/or neurological function deficits and/or mood and mental disturbances in patients suffering from nervous system disorders such as Alzheimer's disease, Parkinson's disease, senile-dementia, multi-infarct dementia, Huntington's disease, mental retardation, Myasthenia Gravis, etc. Additionally, these compounds can be used as reagents in studies on the biochemical mechanism of neurotransmitter based diseases.

The present invention describes a polymorph in substantially pure form. As used herein, "substantially pure" means a compound having a Form 2 purity greater than 90 percent, including 90, 91, 92, 93, 94, 95, 96, 97, 98, 99, and 100 percent.

The present invention is contemplated to be practiced on at least a multigram scale, kilogram scale, multikilogram scale, or industrial scale. "Multigram scale," as used herein, is preferably the scale wherein at least one starting material is present in 10 grams or more, more preferably at least 50 grams or more, even more preferably at least 100 grams or more. "Kilogram scale, us used herein, is intended to mean the scale wherein more than 1000 grams of at least one starting material is used. "Multikilogram scale," as used herein, is intended to mean the scale wherein more than one kilogram of at least one starting material is used. "Industrial scale" as used herein is intended to mean a scale which is other than a laboratory scale and which is sufficient to supply product sufficient for either clinical tests or distribution to consumers.

SYNTHESIS

The methods of the present invention, by way of example and without limitation, may be further understood by reference to Scheme 1. Scheme 1 details the general synthetic method for synthesis of compounds of formula (I) through (VII) where Z is either bromine or chlorine and A is a sulfonyl group.

It is understood that one skilled in the art of organic synthesis could follow the methods described or exemplified herein to prepare homologues of formula III wherein Z is Cl or Br by choosing the appropriate halogenating agent and prepare homologues of formula (VI) by choosing an appropriate sulfonylating agent to react with (V).

SCHEME 1

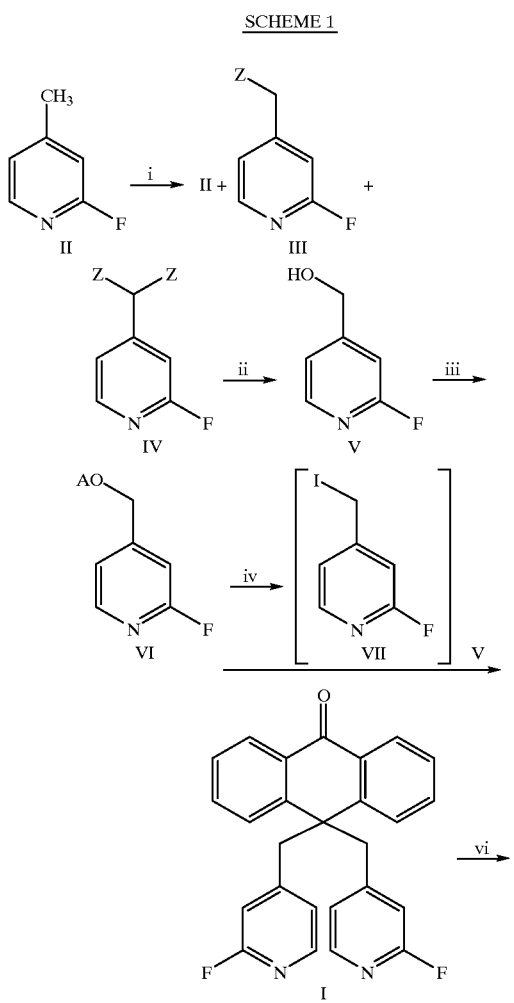

In Step (i), the vessel is charged with 4-methyl-2-flouropyridine, a suitable halogenating agent and enough acetonitrile to dissolve the reactants while maintaining solvent efficiency. The preferred halogenating agents are chlorine, bromine, NCS or NBS. Most preferred is NCS. The amount of halogenating agent used is about 1.0 eq. to about 1.75 eq. Most preferred is about 1.3 to about 1.6 eq. An acceptable amount of solvent is about preferrably 5 mL to about 10 mL per gram of starting material. Most preferred is 5 mL per gram. The vessel is preferably charged with about 0.01 eq. to about 0.2 eq. of a radical initiator. The most preferred amount is about 0.01 to about 0.03 equivalents. While numerous radical initiators are possible, AIBN or benzoyl peroxide are preferred. Most preferred is benzoyl peroxide. A catalytic amount of a suitable acid may be added to accelerate the rate of reaction. The preferred amount of acid is about 0.01 eq. to about 0.10 eq. Most preferred is about 0.04 to about 0.08 eq. Although a large group of acids are possible, organic acids such as formic, acetic, propionic, butanoic, methanesulfonic, p-toluene sulfonic, trifluoroacetic and benzenesulfonic are preferred. Acetic acid is most preferred.

The reaction is preferably refluxed at a suitable temperature for about 0.5 to about 3.0 hours. The preferred reaction time is about 1.0 to about 2.0 hours. Suitable temperatures are about 50° C. to about 100° C. Most preferred is 80° C. to 83° C. The reaction is preferably monitored by HPLC analysis and $^1$H NMR analysis. The reaction is considered complete when HPLC/NMR analysis indicates a maximum amount of monohalogenated material in comparison to the by-products. The preferred product profile is a mixture of about 5% to about 15% unhalogenated starting material, about 65% to about 75% desired product and about 15% to about 25% dihalogenated material. Most preferred is about 9% to 11% unhalogenated starting material, about 68% to about 72% desired product and about 18% to about 22% dihalogenated material. The reaction is quenched by pouring the mixture into water followed by extraction with a suitable organic solvent. While numerous organic solvents are possible, methyl acetate, ethyl acetate, propyl acetate and isopropyl acetate are preferred. Ethyl acetate is most preferred. The organic layer is separated and washed with an aqueous salt solution. The organic layer is then concentrated in vacuo to give the product as a red oil.

In Step (ii) the mixture from Step (i) is preferably taken up in about 15 mL to about 25 mL per gram of water containing a water soluble base. Although numerous bases are possible, lithium carbonate, potassium carbonate and sodium carbonate are preferred. Potassium carbonate is most preferred. The amount of base used is preferably about 1.0 eq. to about 2.0 eq. Most preferred is about 1.2 eq. to about 1.4 eq of base. The solution is preferably heated to about 50° C. to about 100° C. Most preferred is about 80° C. to about 100° C. The reaction is preferably stirred as an oily suspension for about 0.5 to about 3 hours or at which time HPLC analysis preferrably indicates <5% unreacted monochlorinated species remaining. Most preferred is <1% unreacted monochlorinated species remaining. The mixture is cooled to below room temperature with the use of an ice bath, the layers separated, and the organic phase further extracted with water. The combined aqueous extracts are washed with an extraction solvent to remove the unhalogenated and dihalogenated compounds from Step (i), leaving the desired compound behind in the aqueous layer. Extraction solvents may include hydrocarbons ethers or aryls, wherein the hydrocarbon solvents are pentane, hexane, heptane, octane, nonane or decane, ether solvents are diethyl ether, diethoxymethane, ethylene glycol dimethyl ether, ethylene glycol diethyl ether, diethylene glycol dimethyl ether, diethylene glycol diethyl ether, triethylene glycol dimethyl ether, or t-butyl methyl ether, and aryl solvents are benzene, toluene, ethylbenzene, o-xylene, m-xylene or p-xylene. Preferred extraction solvents are pentane, hexane and heptane. The most preferred extraction solvent is hexane. The resultant aqueous layer is extracted with a polar organic solvent to remove the desired benzyl alcohol derivative. Although a large group of polar organic solvents are possible, methyl acetate, ethyl acetate, propyl acetate and isopropyl acetate are preferred. Most preferred is ethyl acetate. The extracts are dried by a suitable method, filtered if a drying agent is used and concentrated in vacuo to give the desired benzyl alcohol derivative. Preferred drying methods include azeotropic distillation and addition of anhydrous agents such as calcium carbonate, sodium sulfate and magnesium sulfate. Most preferred is drying by the addition of anhydrous magnesium sulfate.

In Step (iii), the product from Step (ii) is taken up in a reaction solvent and an acid scavenger is added. Preferred amount of solvent is about 10 mL to about 20 mL per gram of starting material. Most preferred is 15 mL per gram. Preferred acid scavengers are triethyl amine, diisopropyl amine and N-methyl morpholine. Most preferred is triethyl amine. The solution is preferably cooled to about 0° C. to about 5° C. Although numerous reaction solvents are possible, ethyl acetate, acetonitrile, tetrahydrofuran and tert-butyl methyl ether are preferred. Most preferred is ethyl acetate. A suitable sulfonylating agent is preferably added over about 1.0 to about 2.0 hours. Most preferred is about 1.25 to about 1.45 hours. During the addition the temperature is preferably maintained at about 10° C. to about 30° C. Most preferred is about 15° C. to about 25° C. Preferred sulfonylating agents include methanesulfonyl, benzene sulfonyl, trifluoromethanesulfonyl, and p-toluene sulfonyl. Most preferred is methanesulfonyl. The reaction is preferably stirred for about 10 minutes to about 2 hours. Most preferred is about 15 to about 30 minutes. The reaction is considered finished when HPLC analysis preferably indicates the area % of starting material is <5%. Most preferred is when the area of starting material is <1%. Water is added to the mixture and the phases separated. The organic layer is washed with water and saturated salt solution. The solution is dried by a suitable drying method, filtered if a drying agent is used, and concentrated in vacuo. Preferred drying methods include azeotropic distillation and addition of anhydrous agents such as calcium carbonate, sodium sulfate and magnesium sulfate. The most preferred drying method is addition of anhydrous sodium sulfate. The solution is then preferably diluted with a suitable hydrocarbon solvent, cooled to about 0° C. to about 5° C. and stirred for 2 hours resulting in crystals which are filtered and air-dried to give the desired mesylated compound. Suitable hydrocarbon solvents are pentane, hexane, heptane, octane, nonane and decane. Preferred hydrocarbons are hexane, heptane and pentane. Heptane is most preferred.

The resulting residue can then be recrystallized from a suitable recrystallization solvent to give the purified compound. Appropriate solvents for recrystallization are readily understood by one skilled in the art.

In Step (iv), the product from Step (iii) is stirred in an appropriate reaction solvent and an iodine salt is added. While numerous reaction solvents are possible, tetrahydrofuran and acetone are preferred. Most preferred is tetrahydrofuran. Preferred iodine salts include lithium iodide, sodium iodide and potassium iodide. Most preferred is sodium iodide. The preferred amount of iodine salt is about 0.5 eq. to about 1.0 eq. Most preferred is about 0.2 eq. to about 0.5 eq. of iodine salt. The solution is stirred for about 1 hour to about 3 hours at about 0° C. to about 40° C., and for about 15 minutes to about 45 minutes at about 20° C. to 45° C. Most preferred is stirring the solution for about 1.5 hour to about 2.5 hours at about 5° C. to about 25° C., and for about 25 minutes to about 35 minutes at about 25° C. to 35° C. The solution is preferably concentrated in vacuo and the resulting oil mixed with water, a suitable hydrocarbon solvent, a suitable organic solvent and a thiosulfate solution. Preferred hydrocarbon solvents are pentane, heptane and hexane. Most preferred is heptane. Preferred organic solvents are methyl acetate, ethyl acetate and isopropyl acetate. Most preferred is ethyl acetate. The organic phase is separated and preferably the aqueous layer is further extracted with a 1:1 hydrocarbon/acetate mixture. The most preferred hydrocarbon is heptane; the most preferred acetate is ethyl acetate. Preferably, the combined organic extracts are dried over a suitable drying agent, filtered if a drying agent is used, and the solution concentrated in vacuo and the resulting oil placed under vacuum to remove residual solvent. Preferred drying methods include azeotropic distillation and addition of anhydrous agents such as calcium carbonate, sodium sulfate and magnesium sulfate. Most preferred is drying by the addition of anhydrous magnesium sulfate.

The stability of this benzyl iodide intermediate is to be considered when addressing the use of the isolated compound and will be readily understood by one skilled in the art. If it is not necessary to isolate the intermediate, it is recommended that the benzyl iodide be generated in-situ as described in Step (v).

In Step (v), two solutions are prepared. For one, a base solution preferably with a concentration of about 0.8 M to about 1.2 M is prepared by the addition of a suitable strong base to a suitable reaction solvent. The most preferred base solution molarity is about 0.9 M to about 1.1 M. Although a large group of strong bases are possible, tertiary alkoxides such as lithium tert-butoxide, potassium t-butoxide and sodium tert-butoxide are preferred. Lithium t-butoxide is most preferred. While numerous reaction solvents are possible, tetrahydrofuran, 1,4 dioxane, ethylene glycol dimethyl ether, ethylene glycol diethyl ether and t-butyl methyl ether are preferred. Most preferred is tetrahydrofuran. This base solution is preferably added to anthrone in a suitable reaction solvent at about 5° C. to about 40° C. to form the anionic anthrone salt. Most preferred is about 15° C. to 30° C. Preferred reaction solvents are tetrahydrofuran, 1,4 dioxane, ethylene glycol dimethyl ether, ethylene glycol diethyl ether and t-butyl methyl ether. Most preferred is tetrahydrofuran. The second solution is prepared by mixing the product from Step (iii) with a suitable iodinating agent in a suitable reaction solvent at a temperature of about 25° C. to about 50° C. for about 1 hour to about 5 hours to partially form the benzyl iodide. Most preferred is about 2 hours to about 4 hours. Most preferred temperature is about 35° C. to about 45° C. The lithio anthrone solution described is preferably added dropwise over about 30 minutes to 2 hours at a temperature of about 30° C. to 60° C. to the iodide/mesylate solution. Most preferred is about 1 hour to about 2 hours. Most preferred temperature is about 40° C. to about 50° C. The reaction is preferably stirred for a reaction time of about 30 minutes to about 2 hours or until HPLC peak area of dialkylated anthrone is continuous, and the mesylated compound from Step (iii) is preferably <5% by area. Most preferred is <1%. Most preferred reaction time is about 45 minutes to about 90 minutes. The solution is preferably washed with an aqueous salt solution and the volatiles are removed in vacuo. The residue is preferably diluted with a suitable aryl solvent and heated to about 80° C. to about 110° C., cooled to about 75° C. to 95° C. and stirred with basic alumina. The solution is preferably filtered through a Celite pad, concentrated by atmospheric distillation at about 20° C. to about 30° C. to crystallize the product. Further crystallization can be induced by the dropwise addition of a hydrocarbon solvent followed by cooling to about 0° C. for about 1–3 hours. Heptane is the preferred solvent. The crystals are preferably collected by filtration, washed with a additional hydrocarbon solvent and dried at 60° C. in vacuo to yield the product.

In Step (vi), the desired polymorph is produced in substantially pure form. The product of Step (v) is preferably heated to about 50° C. to about 90° C. to affect complete dissolution of the compound. Most preferred is about 75° C. to about 85° C. The most preferred solvent for the recrystallization is isopropyl alcohol which is most preferably heated to reflux. The solution is then preferably cooled about 5° C. to about 20° C. below reflux temperature and clarified through a filter such as a Celite pad. The solution is concentrated, preferably by atmospheric distillation and cooled to about 0° C. to about 10° C. over about 1 to about 4 hours. The crystals are preferably collected by filtration, washed with cold recrystallization solvent and dried to give Form 2 crystals. The product may be slurried with refluxing hydrocarbons for about 4 to about 8 hours, cooled to about 5° C. to about 20° C. below the reflux temperature, and filtered. The preferred hydrocarbon is cyclohexane. The filter cake is preferably washed with hydrocarbons heated to about 60° C. to 80° C. and dried at about 60° C. in vacuo. This hydrocarbon treatment is intended to remove 1–5% of any remaining anthrone, bianthrone and 1,2-di(2-fluoro-4-pyridyl)ethylene present as low-level impurities. The final purity of the form 2 compound is preferably >95%, More preferably the purity is >98%, and a purity of >99% is most preferred.

The present invention may be further exemplified by reference to Scheme 2 wherein Z is Cl, and A is methane sulfonyl.

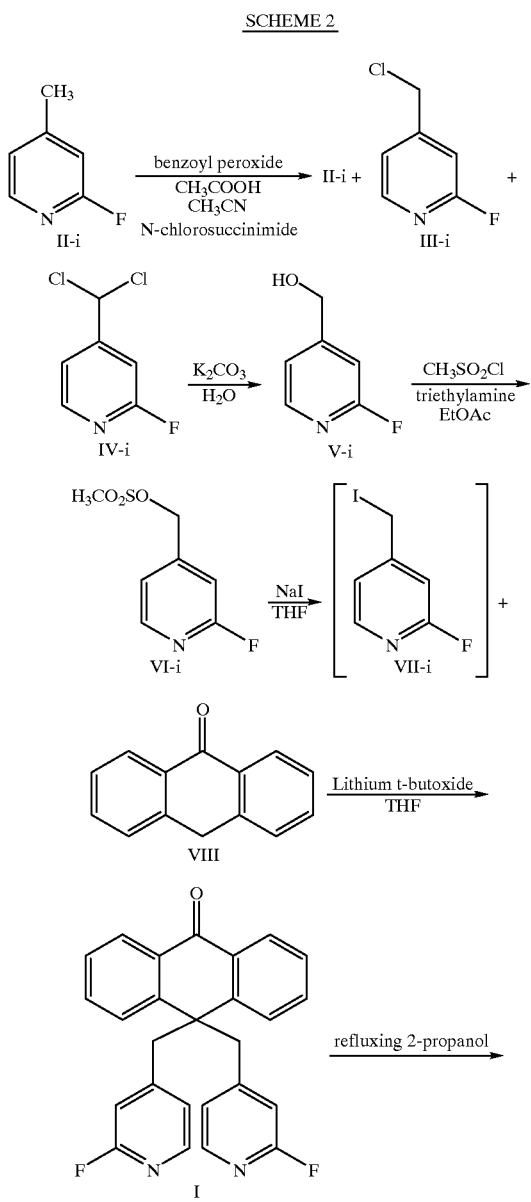

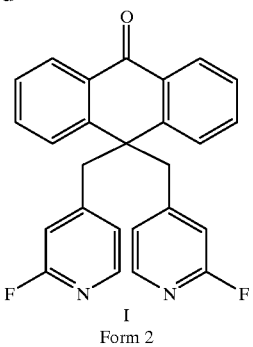

Form 2

The preparation of Form 1 can be accomplished by methods described in U.S. Pat. No. 5,594,001 (Teleha, C. A.; Wilkerson, W. W.; Earl, R. A.). Recrystallization from dilute solutions in 2-propanol yields the Form 2 polymorph. Form 1 and Form 2 may be readily distinguished by X-ray powder diffraction and differential scanning calorimetry (DSC). The X-ray diffractograms of the Form 1 and Form 2 polymorphs are shown in FIG. 1 and 2 respectively. The main peaks in the diffractogram for the Form 2 polymorph occur at 2θ values of about 5.8, 7.8, 10.7, 12.6, 16.4, 18.3, 19.8, 22.5, 24.9, 28.9, and 39.1. The relative intensities of the peaks may vary, depending upon the sample preparation technique, the sample mounting procedure and the particular instrument employed. Moreover, instrument variation and other factors may affect the 2θ values, therefore, the peak assignments may vary by plus or minus 0.2.

Form 2 can also be distinguished from Form 1 by differential scanning calorimetry (DSC). Form 1 has a melting point from about 154° C. to about 156° C. Form 2 has a melting point of about 168° C. to about 172° C. Conversion from Form 1 to Form 2 can be seen during the course of heating if the Form 1 is seeded with the more stable Form 2. The thermograms of Forms 1 and 2 are shown in FIG. 3 and 4 respectively.

Dosage and Formulation

Compounds of this invention can be administered to treat cognitive disorders and/or neurological function deficits and/or mood and mental disturbances by any means that produces contact of the active agent with the agent's site of action in the body of a mammal or patient. The compounds can be administered by any conventional means available for use in conjunction with pharmaceuticals either as individual therapeutic agents or in combination of therapeutic agents. They can be administered alone, but are generally administered as a pharmaceutical composition comprised of a compound and a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and the desired effect. For use in the treatment of said diseases or conditions, the compounds of this invention can be orally administered daily at a dosage of the active ingredient of 0.001 to 100 mg/kg of body weight. Ordinarily, a dose of 0.01 to 10 mg/kg/day in divided doses one to four times a day, or in sustained release formulation was effective in obtaining the desired pharmacological effect.

Dosage forms (pharmaceutical compositions) suitable for administration contain from about 0.025 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets, and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film coated to mask any unpleasant taste, or used to protect the active ingredients from the atmosphere, or to allow selective disintegration of the tablet in the gastrointestinal tract.

Liquid dosage forms for oral administration can contain coloring and flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Anti-oxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in *"Remington's Pharmaceutical Sciences"*,. A. Osol, a standard reference ion this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg lactose, 50 mg cellulose, and 6 mg magnesium stearate.

Soft Gelatin CaDsules

A mixture of active ingredient in a digestible oil such as soybean, cottonseed oil, or olive oil was prepared and injected by means of a positive displacement was pumped into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed absorption.

Injectable

A parenteral composition suitable for administration by injection is prepared by dissolving 1.5% by weight of active ingredient in a solution containing 10% by volume of propylene glycol in water. The solution is sterilized by commonly used techniques.

Suspension

An aqueous suspension is prepared for oral administration so that each 5 milliliters contains 25 milligrams of finely divided active ingredients, 200 milligrams of sodium carboxymethyl cellulose, 5 milligrams of sodium benzoate, 1.0 gram of sorbitol solution, U.S.P., and 0.025 milliliter of vanillin.

Nasal Spray

An aqueous solution is prepared such that each 1 milliliter contains 10 milligrams of active ingredient, 1.8 milligrams methylparaben, 0.2 milligram propylparaben and 10 milligrams methylcellulose. The solution is dispensed into 1 milliliter vials.

Luna Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

The foregoing disclosure includes all the information deemed essential to enable those of skill in the art to practice the claimed invention. Because the cited applications may provide further useful information these cited materials are hereby incorporated by reference.

The following examples are meant to be illustrative of the present invention. These examples are presented to exemplify the invention and are not to be construed as limiting the inventors scope.

Example 1

4-chloromethyl-2-fluoropyridine (III-i) A mixture of II-i (50.0 g, 0.446 mol) acetonitrile (250 mL) N-chlorosuccinimide (88.4 g, 0.67 mol) benzoyl peroxide (2.15 g, 9 mmol) and acetic acid (1.5 mL, 25 mmol) were refluxed for 90 min. HPLC and $^1$H NMR analysis indicated a 69% yield of III-i, 17% of IV-i, and 12% of remaining unreacted II-i (the yield of III-i peaked at 71% after 80 min at reflux). The mixture was poured into water (200 mL) and extracted with EtOAc (200 mL). The organic layer was separated, washed with 5% aqueous NaCl solution (2×400 mL) and concentrated in vacuo at 35° C. to 62.2 g of red oil. This mixture was hydrolyzed as described in the next step without further purification. An analytical sample was prepared by the chlorination of V-i as follows. A solution of VI-i (3.0 g, 14.5 mmol) NaCl (9.0 g, 0.15 mol) 2N HCl (6.0 mL water (15 mL) and acetone (150 mL) was refluxed for 3 h. The cooled mixture was mixed with water (200 mL) and EtOAc (100 mL). The organic phase was separated, washed with water (50 mL) and dried over $MgSO_4$. The solution was concentrated in vacuo and vacuum distilled; the fraction boiling at 70–72° C. (3.5 mmHg) collected to yield 1.3 g (61%) of colorless oil. $^1$H NMR: 8.22(d, J=5.1 Hz, 1H), 7.21(d, J=5.1 Hz, 1H), 6.99(s, 1H), 4.57 (s, 3H). $^{13}$C NMR: 164.0 (d, J=239.2 Hz), 151.5 (d, J=8.1 Hz), 148.0 (d, J=15.1 Hz), 120.6 (d, J=4.5 Hz), 108.8 (d, J=38.8 Hz), 43.2 (d, J=3.5 Hz); $^{19}$F NMR: −67.8; MS: m/e 146(M+1); Anal. Calcd for $C_6H_5ClFN$: C, 49.51; H, 3.46; N, 9.62; F, 13.05. Found: C, 49.31; H, 3.56; N, 9.32; F, 12.84.

Example 2

2-Fluoro-4-hydroxymethylpyridine (V-i) Impure III-i (62.2 g, 0.31 mol) water (700 mL) and potassium carbonate (56.0 g, 0.41 mol) was heated as a stirred oily suspension for 2 hours (HPLC indicated <1% unreacted III-i remaining). The mixture was cooled, the layers separated, and the lower, organic phase further extracted with water (100 mL). The combined aqueous extracts were washed with heptane (50 mL) and extracted with EtOAc (4×400 mL). The extracts were dried over $MgSO_4$ and concentrated in vacuo to 24.8 g (62%) of white solids (98 HPLC area %). An analytical sample was prepared by recrystallization from 1:1 EtOAc/heptane (5 mL/g) to produce colorless needles. mp 59.3–60.4° C.; $^1$H NMR: 8.07 (d, J=5.1 Hz, 1H), 7.15 (d, J=5.1 Hz, 1H), 6.98 (s, 1H), 4.77 (d, J=5.4 Hz, 2H), 4.26 (br s, 1H); $^{13}$C NMR: 164.0 (d, J=239.6 Hz), 157.1 (d, J=7.6 Hz), 146.9 (d, J=14.1 Hz), 118.7 (d, J=4.0 Hz), 106.5 (d, J=37.2 Hz), 62.5 (d, J=3.0 Hz); $^{19}$F NMR: −68.8. MS: m/e 128(M+1). Anal. Calcd for $C_6H_6FNO$: C, 56.69; H, 4.76; F, 14.95; N, 11.01. Found: C, 56.66; H, 4.63; F, 14.74; N, 11.03.

Example 3

2-Fluoro-4-hydroxymethylpyridine, methanesulfonate (VI-i) A solution of V-i (170 g, 1.34 mol) EtOAc (2.6 L) and triethylamine (270 mL, 1.94 mol) was cooled to 0–5° C. and methanesulfonyl chloride (130 mL, 1.68 mol) was added over 100 min while maintaining the temperature at <20° C. The reaction was aged for another 10 min (HPLC indicated the area % of 6 was <1%). The mixture was mixed with water (350 mL) and the phases were separated. The organic layer was washed with water and saturated brine (each 400 mL). The solution was dried over anhydrous $Na_2SO_4$, filtered, and concentrated in vacuo to approximately a volume of 900 mL. This solution was diluted with heptane (600 mL) cooled to 0–5° C. and stirred for 2 h. The crystals were filtered and air-dried to 251 g (88%) of pale yellow crystals (>97 HPLC wt % purity versus a reference standard). An analytical sample was prepared by recrystallization from 1:1 EtOAc/heptane (15 mL/g). mp=58.3–59.1° C.; $^1$H NMR: 8.27 (d, J=5.4 Hz, 1H), 7.20 (d, J=5.1 Hz, 1H), 6.98 (s, 1H), 5.26 (s, 2H), 3.10 (s, 3H); $^{13}$C NMR (DMSO-$d_6$): 163.2(d, J=235.2 Hz), 150.0(d, J=8.6 Hz), 148.0(d, J=15.6 Hz), 120.3(d, J=3.5 Hz), 107.7(d, J=38.2 Hz), 68.3(d, J=3.0 Hz), 37.0; $^{19}$F NMR: −66.84; MS: m/e 206(M+1). Anal. Calcd for $C_7HBFNO3S$: C, 40.96%; H, 3.93%; F,9.26%; N, 6.82%; S, 15.62%. Found C, 41.00%; H, 3.81%; F, 9.47%; N, 6.70%; S, 15.76%.

Example 4

2-Fluoro-4-iodomethylpyridine (VII-i) A solution of 36.0 g (0.18 mol) of V-i, sodium iodide (39.4 g, 0.26 mol) and acetone (1.0 L) was stirred for 2 h at 5–20° C. and at 30° C. for 30 min. The solution was concentrated in vacuo and the resulting oil was mixed with water (300 mL), heptane (50 mL) EtOAc (50 mL) and saturated sodium thiosulfate (5 mL). The organic phase was separated and the aqueous layer further extracted with 1:1 heptane/EtOAc (100 mL). The combined organic extracts were dried over anhydrous $MgSO_4$, the solution concentrated in vacuo and the resulting oil freed of remaining solvents in vacuo to produce 40.3 g (97%) of reddish orange oil (99.8 HPLC area %, same conditions as indicated in the Experimental/General section). The $^1$H NMR spectrum did not show any impurities. $^1$H NMR (300 MHz, $CDCl_3$): 8.12(d, J=5.1 Hz, 1H), 7.13(d, J=5.1 Hz, 1H), 6.88(s, 1H), 4.31(s, 2H); 13C NMR (75.4 MHz, $CDCl_3$): 163.8(d, J=237.9 Hz), 153.5(d, J=8.2 Hz), 148.1(d, J=15.5 Hz), 121.3(d, J 4.6 Hz), 109.2(d, J=38.0 Hz), 46.6; $^{19}$F NMR (376 MHz, $CDCl_3$): −68.1; MS: m/e 238(M+H).

Example 5

10,10-Bis[(2-fluoro-4-pyridinyl)methyl]-9(10H)-anthracenone (I) Two solutions are prepared. For one, 1.0 M lithium t-butoxide in THF (1.00 L, 1.00 mol) was added to a solution of anthrone (70.0 g, 0.36 mol) in THF (0.70 L) at 15–30° C. to form lithio anthrone. The second solution was prepared by mixing sodium iodide (45.0 g, 0.30 mol) VI-i (150.0 g, 0.73 mol) and THF (1.60 L) at 40° C. for 3 h to form a mixture of VI-i/VII-i. The lithio anthrone solution was added dropwise over 100 min at 40–50° C. to the iodide/mesylate solution. The reaction was aged for 1 h (the HPLC peak area of VII-i was <1%). The solution was washed with saturated aqueous brine (2×0.90 L). Volatiles were removed in vacuo and the residue was diluted with toluene (1.3 L). The solution was heated to 100° C., cooled to 90° C. and stirred with basic alumina (120 g) for 30 min. The solution was filtered through a Celite pad, concentrated by atmospheric distillation to 500 mL and cooled to 25° C. to crystallize I. Further crystallization was induced by the dropwise addition of n-heptane (0.60 L) followed by cooling to 0° C. for 2 h. The crystals were collected by filtration, washed with n-heptane (0.2 L) and dried at 60° C. in vacuo to yield 121 g of I (75% yield from anthrone, 92 HPLC wt % purity versus a reference standard).

Example 6

Recrystallization to give Form II 10, 10-Bis[(2-fluoro-4-pyridinyl)methyl]-9(10H)-anthracenone Two lots preparared as described were combined (238.0 g) and dissolved into refluxing IPA (3.80 L) cooled slightly below reflux and filtered through a Celite pad. The solution was concentrated by atmospheric distillation to 1.90 L and cooled to 0° C. over 3 h. The crystals were collected by filtration, washed with 0° C. IPA (0.2 L) and dried as above to give 208 g of crystals. Part of this (180g) was slurried with refluxing cyclohexane (4.5 L) for 6 h, cooled to 75° C. and filtered. The cake was washed with cyclohexane (0.25 L) at 70° C. and dried at 60° C. in vacuo to 167 g. (This hydrocarbon treatment removes 1–5% of remaining anthrone, bianthrone and 1,2-di(2-fluoro-4-pyridyl)ethylene present as low-level impurities).

Three identical preparations were combined (327 g), dissolved into IPA (3.50 L) at 75° C., treated with Darco G-60 (52 g) and stirred for 30 min. The suspension was filtered through a pad of Celite. The filtrate was concentrated to 2.60 L by atmospheric distillation and cooled to 0° C. The crystals were filtered, washed with 0° C. IPA (200 ml), dried in vacuo at 50° C. and ground in a mortar and pestle to 284 g (yield 56%) of Form II polymorph, HPLC peak area=

99.94%, HPLC wgt % assay: >99.9%, mp 169° C., $^1$H NMR (400 MHz, DMSO-$d_6$): 8.42(2H, dd, J=0.9, 7.7 Hz), 7.95 (2H, dd, J=1.5, 7.7 Hz), 7.93(2H, ddd, J=1.5, 7.7, 7.7 Hz), 7.65(2H, d, J=5.2 Hz), 7.53(1H, ddd, J=0.9, 7.7, 7.7 Hz), 6.11(2H, ddd, J=5.2, 1.4, 2.3 Hz), 5.92(2H, dd, J=1.4 Hz, J=1.3 Hz), 3.95(4H, s); 13C NMR (100.6 MHz, DMSO-$d_6$): 181.7, 162.3(d, J=235.0 Hz), 152.1(d, J=7.6 Hz), 146.4(d, J=16.0 Hz), 144.1, 134.0, 131.7, 128.5, 128.0, 126.5, 122.6, 109.7(d, J=37.4 Hz), 47.9, 47.5(d, J=2.3 Hz); $^{19}$F NMR (376.1 MHz, DMSO-$d_6$): −70.56; HRMS (ESI): 413.144623 (calcd 413.146545 for $C_{26}H_{19}N_2OF_2$): IR (KBr): 3060, 2946, 1665, 1602, 1556, 1475, 1452, 1407, 1321, 1269, 1149, 931, 839, 776, 702, 645 cm$^{-1}$. Anal. calcd. for $C_{26}H_{18}F_2N_2O$: C, 75.72; H, 4.40; F, 9.21; N, 6.79. Found: C, 75.70; H, 4.34; F, 9.21; N, 6.78.

$^1$H NMR spectra were determined at 300 MHz, $^{13}$C NMR at 75.4 MHz, and $^{19}$F NMR at 282 MHz, all in CDCl$_3$, unless otherwise specified. $^{19}$F NMR spectra are run with CFCl$_3$ as an internal reference. Mass spectra (MS) were obtained by ammonia chemical ionization. Elemental analyses were performed at Quantitative Technologies Inc., Whitehouse, N.J. Melting points are uncorrected. Solvent mixtures are defined by volume (v/v). All solvents except for tetrahydrofuran (anhydrous) were reagent grade and were not further purified. All reactions were carried out under a positive pressure of nitrogen unless otherwise specified. Reagents and solvents were used as received unless otherwise noted. 2-Fluoro-4-methylpridine was purchased from Lancaster Chem. Co. Solutions of lithium t-butoxide were purchased from Aldrich Chem. Co. HPLC: Zorbax 4.6 mm×15 cm RX C18 column at 1.00 mL/min at 40° C. and 260 nm. Solvent A: water; Solvent B: CH$_3$CN. Solvent program: A/B 60/40 at t=0 min, 40/60 at t=10 min, 15/85 at t=15 min, 40/60 at t=18 min, 60/40 at t=20 min. Retention times: 1, $t_r$=8.2 min; 2, $t_r$=3.5 min; 3, $t_r$=4.1 min; 4, $t_r$=6.1 min; 5, $t_r$=1.7 min; 6, $t_r$=2.6 min; 7, $t_r$5.2 min.

Although the present invention has been described with respect to specific embodiments, the details of these embodiments are not to be construed as limitations. Various equivalents, changes and modifications may be made without departing from the spirit and scope of this invention, and it is understood that such equivalent embodiments are part of this invention. The present invention may be embodied in other specific forms without departing for the spirit or essential attributes thereof and, accordingly, reference should be made to the appended claims as further indicating the scope of the invention.

What is claimed is:

1. The Form 2 polymorph of crystalline 10,10-Bis((2-fluoro-4-pyridinyl)methyl)-9(10H)-anthracenone.

2. The Form 2 polymorph of claim 1, having an x-ray powder diffraction pattern comprising four or more 2θ values selected from the group consisting of 5.8±0.2, 7.8±0.2, 10.7±0.2, 12.6±0.2, 16.4±0.2, 18.3±0.2, 19.8±0.2, 22.5±0.2, 24.9±0.2, 28.9±0.2, and 39.1±0.2.

3. The Form 2 polymorph of claim 1, having an x-ray powder diffraction pattern substantially in accordance with that shown in FIG. 2.

4. The Form 2 polymorph of claim 1, having a differential scanning calorimetry thermogram having a peak at about 168° C. to about 172° C.

5. The Form 2 polymorph of claim 1, prepared by recrystallization of 10,10-Bis((2-fluoro-4-pyridinyl)methyl)-9(10H)-anthracenone from an alcoholic solvent.

6. The Form 2 polymorph of claim 5, wherein the alcoholic solvent is isopropanol.

7. A pharmaceutical composition comprising a therapeutically effective amount of the polymorph of claim 1 and a pharmaceutically acceptable carrier.

8. A method for the treatment of cognitive or neurological dysfunction comprising administering to a host in need thereof a therapeutically effective amount of the polymorph of claim 1.

* * * * *